US008287602B2

(12) United States Patent
Daignault et al.

(10) Patent No.: US 8,287,602 B2
(45) Date of Patent: Oct. 16, 2012

(54) URINARY STENT

(75) Inventors: Kenneth J. Daignault, Holden, MA (US); Alfred Intoccia, Nashua, NH (US); Richard Tah, Framingham, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 562 days.

(21) Appl. No.: 12/331,648

(22) Filed: Dec. 10, 2008

(65) Prior Publication Data

US 2009/0156977 A1 Jun. 18, 2009

Related U.S. Application Data

(60) Provisional application No. 61/013,034, filed on Dec. 12, 2007.

(51) Int. Cl.
*A61F 2/04* (2006.01)
(52) U.S. Cl. ................. 623/23.66; 623/23.65; 623/23.64
(58) Field of Classification Search ............... 623/23.66
See application file for complete search history.

(56) References Cited

U.S. PATENT DOCUMENTS

| 4,893,623 | A | 1/1990 | Rosenbluth |
| 5,035,706 | A | 7/1991 | Giantureo et al. |
| 5,207,672 | A | 5/1993 | Roth et al. |
| 5,246,445 | A | 9/1993 | Yachia et al. |
| 5,322,501 | A | 6/1994 | Mahmud-Durrani |
| 5,499,994 | A | 3/1996 | Tihon et al. |
| 5,588,965 | A | 12/1996 | Burton et al. |
| 6,119,045 | A * | 9/2000 | Bolmsjo ...................... 607/156 |
| 6,395,021 | B1 | 5/2002 | Hart et al. |
| 6,607,477 | B1 | 8/2003 | Longton et al. |
| 6,685,734 | B1 | 2/2004 | Välimaa et al. |
| 6,733,536 | B1 | 5/2004 | Gellman |
| 6,929,651 | B2 | 8/2005 | Huxel et al. |
| 6,929,663 | B2 | 8/2005 | Rioux et al. |
| 6,981,964 | B2 * | 1/2006 | Rioux et al. .................. 604/107 |
| 7,041,090 | B2 | 5/2006 | Bolmsjö et al. |
| 7,044,980 | B2 * | 5/2006 | Hammond et al. ........ 623/23.66 |
| 7,108,655 | B2 | 9/2006 | Whalen et al. |
| 7,141,038 | B2 | 11/2006 | Whalen et al. |
| 2004/0181235 | A1 * | 9/2004 | Daignault et al. ............ 606/108 |
| 2004/0193283 | A1 * | 9/2004 | Rioux et al. ............... 623/23.66 |
| 2005/0113933 | A1 * | 5/2005 | Carter et al. .................. 623/23.7 |
| 2006/0079952 | A1 | 4/2006 | Kaplan et al. |
| 2006/0206096 | A1 * | 9/2006 | Accisano et al. ............. 604/540 |
| 2006/0259151 | A1 | 11/2006 | Ward |

* cited by examiner

*Primary Examiner* — David Isabella
*Assistant Examiner* — Jacqueline Woznicki
(74) *Attorney, Agent, or Firm* — Brown Rudnick LLP

(57) ABSTRACT

A urinary stent includes an elongate member that defines a lumen extending therethrough and that is configured to be disposed at least partially within a prostatic portion of a urethra of a patient. The elongate member includes a collapsible portion disposed at a proximal end portion of the elongate member. The collapsible portion has a first configuration in which an outer perimeter at a proximal end of the collapsible portion is substantially equal to an outer perimeter of a remaining portion of the elongate member and a second configuration in which the outer perimeter at the proximal end of the collapsible portion is smaller than the outer perimeter of the remaining portion of the elongate member.

10 Claims, 8 Drawing Sheets

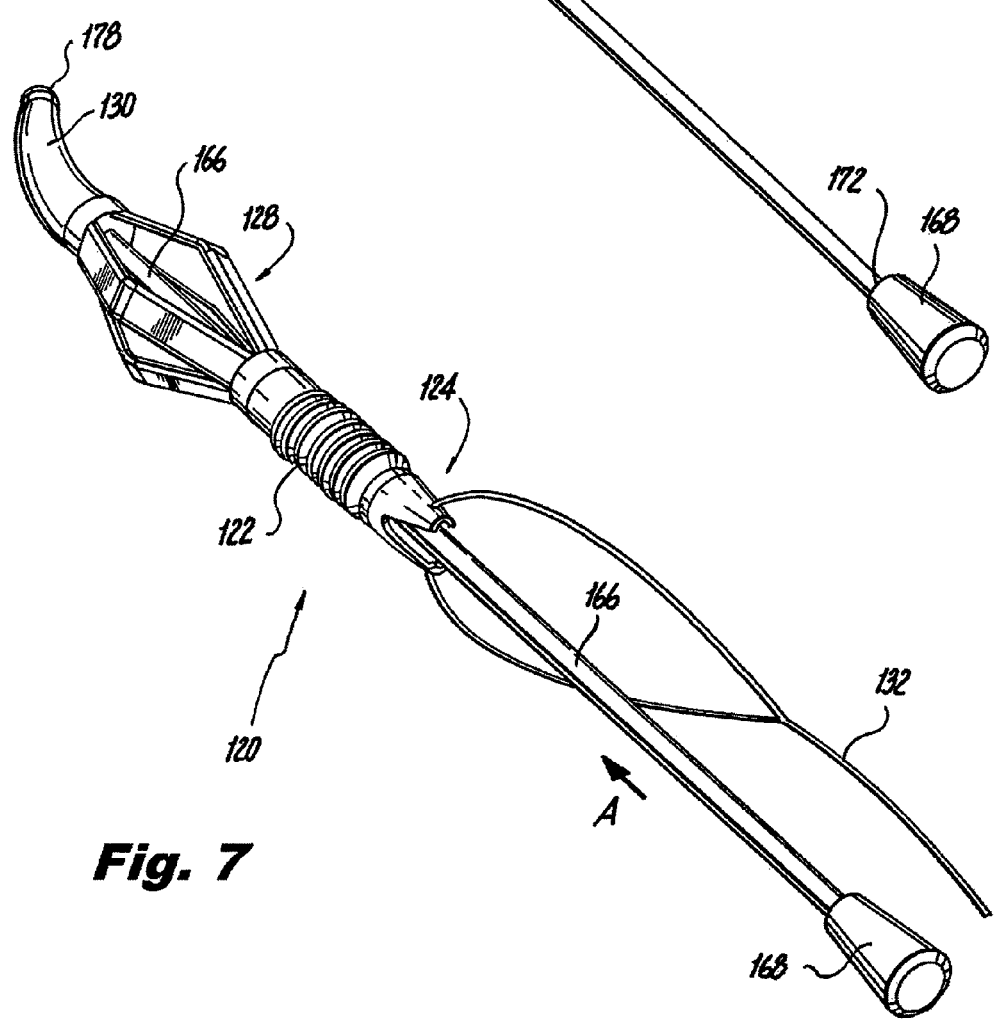

URINARY STENT

CROSS-REFERENCE TO RELATED CASES

This application claims priority to, and the benefit of Provisional U.S. Patent Application Ser. No. 61/013,034, filed Dec. 12, 2007, the entirety of which is incorporated herein by reference.

TECHNICAL FIELD

The invention relates generally to medical devices and more particularly to a urinary stent. The stent can allow fluid drainage from a bladder and through a urethra of a patient.

BACKGROUND INFORMATION

The male urethra is generally a tubular passageway extending from the bladder to the end of the penis. As urine travels from the bladder and out of the body, the urine passes through four sections of the urethra referred to as the prostatic urethra, the membranous urethra, the bulbar or bulbous urethra, and the pendulous or distal urethra. Surrounding the prostatic urethra and below the bladder is a prostate gland. In some men, especially men over fifty years of age, the prostate can become swollen or enlarged due to disease or infection. The enlarged prostate can constrict the urethra causing discomfort and/or bladder outlet obstruction.

Medical devices, such as urethral stents, are typically used to facilitate fluid flow from a bladder and through a urethra. Urethral stents are designed to hold open one or more of the sections of the urethra obstructing the flow of urine, such as constricted portions caused by a swollen or enlarged prostate. The size or outer perimeter of a stent that is needed to maintain the urethra in an open state can sometimes result in difficulty removing the stent from the patient's body.

SUMMARY OF THE INVENTION

The invention relates generally to a urinary stent, such as a male urethral stent, for at least partial placement in a prostate portion of a urethra of a patient, and the stent includes a removal mechanism to allow the stent to be removed easily from the urethra of the patient.

In one aspect, the invention involves a urinary stent that includes an elongate member that defines a lumen extending therethrough and that is configured to be disposed at least partially within a prostatic portion of a urethra of a patient. The elongate member includes a collapsible portion disposed at a proximal end portion of the elongate member. The collapsible portion has a first configuration in which an outer perimeter at a proximal end of the collapsible portion is substantially equal to an outer perimeter of a remaining portion of the elongate member. The collapsible portion has a second configuration in which the outer perimeter at the proximal end of the collapsible portion is smaller than the outer perimeter of the remaining portion of the elongate member.

Embodiments according to this aspect of the invention can include the following features. The collapsible portion can be frusto-conical in shape when in the second configuration. The collapsible portion can be formed monolithically with the elongate member. The collapsible portion can define an opening at a proximal end of the collapsible portion, and the opening can have a first diameter in the first configuration and a second smaller diameter in the second configuration. The collapsible portion can include a first arm and a second arm, where the first arm and the second arm each define an opening at a proximal end of the collapsible portion. In some embodiments, the urinary stent can further include a second portion that extends from the elongate member opposite the collapsible portion and that is configured to be disposed at least partially within a bladder of the patient.

In another aspect, the invention involves a urinary stent that includes an elongate member defining a lumen extending therethrough and that is configured to be disposed at least partially within a prostatic portion of a urethra of a patient. The elongate member includes a collapsible portion disposed at a proximal end portion of the elongate member. The collapsible portion defines an opening at a proximal end of the collapsible portion in communication with the lumen and has a first configuration in which the opening is substantially open. The collapsible portion has a second configuration in which the collapsible portion is at least partially collapsed and the opening is at least partially closed such that at least part of the collapsible portion is smaller at its outer perimeter than an outer perimeter of the rest of the elongate member. The urinary stent also includes a second portion extending from the elongate member opposite the collapsible portion and that is configured to be disposed at least partially within a bladder of the patient.

Embodiments according to this aspect of the invention can include the following features. The collapsible portion can be frusto-conical in shape when in the second configuration. The collapsible portion can be formed monolithically with the elongate member. The opening can have a first diameter in the first configuration and a second smaller diameter in the second configuration. The collapsible portion can include a first arm and a second arm, and the first arm and the second arm define the opening. The second portion can have a collapsed configuration for insertion into the bladder, and an expanded configuration for retaining the second portion within the bladder.

In yet another aspect, the invention involves a urinary stent that includes an elongate member that defines a lumen extending between a proximal end and a distal end of the elongate member. The elongate member is configured to be disposed at least partially within a prostatic portion of a urethra of a patient and includes a tapered proximal end portion that defines an opening on a proximal end of the elongate member. The opening is in communication with the lumen of the elongate member to facilitate fluid flow therethrough. A second portion extends from the elongate member opposite the tapered, proximal end portion and is configured to be disposed at least partially within a bladder of the patient.

Embodiments according to this aspect of the invention can include the following features. The second portion can be coupled to the elongate member. The tapered proximal end portion can be formed monolithically with the elongate member. The tapered proximal end portion can be frusto-conical in shape and define the opening as a substantially fixed size opening. The second portion can have a collapsed configuration for insertion into the bladder and an expanded configuration for retaining the second portion within the bladder. The urinary stent can further include a tether coupled to the tapered proximal end portion, and the tether extends proximal from the elongate member.

For a fuller understanding of the nature and operation of various embodiments according to the invention, reference is made to the drawings briefly described in next section and also to the more detailed description that follows the brief description of the drawings. The drawings should be considered in conjunction with the following more detailed description. In the drawings, the same or similar reference numbers generally denote the same or similar elements of the various disclosed embodiments. The drawings are not necessarily to scale, emphasis instead generally being placed on conveying certain concepts and aspects according to the invention.

BRIEF DESCRIPTION OF THE DRAWINGS

FIG. 6 is a side view of a pushing device according to one embodiment.

FIG. 7 is a side perspective view of the stent of FIG. 2 shown with the pushing device of FIG. 6 disposed therein.

DESCRIPTION

Figure 1:
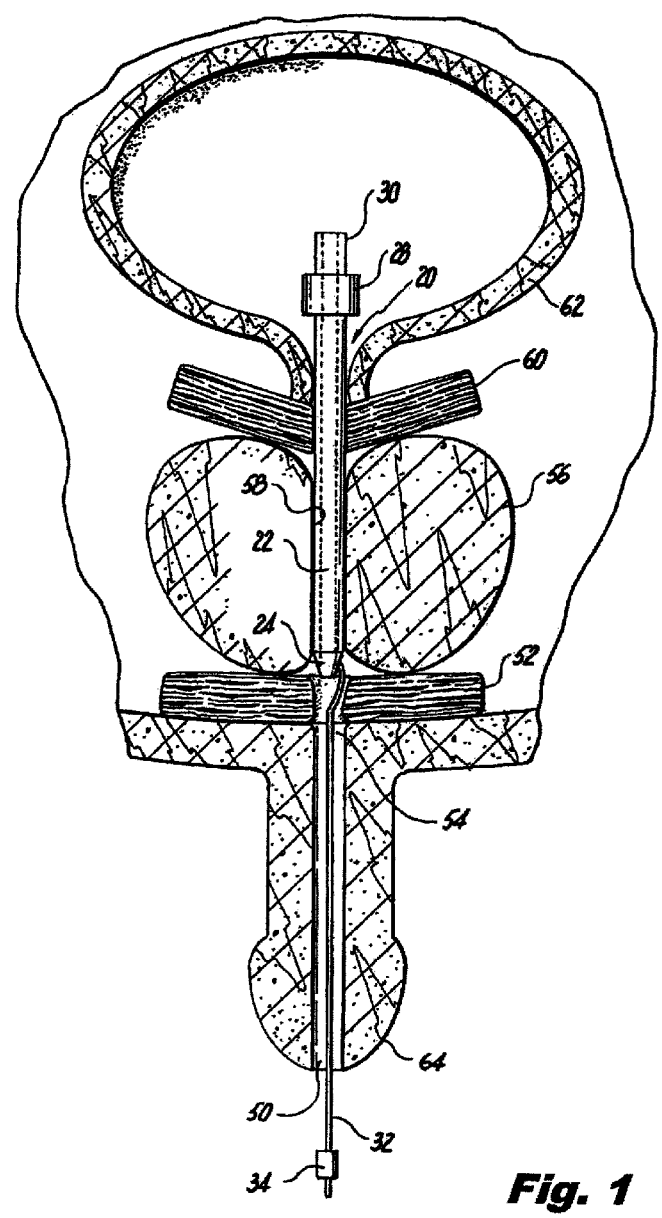
FIG. 1 is a schematic illustration of an embodiment of a delivery device and implant.

The medical devices and methods described herein are generally directed to a urinary stent that can be at least partially inserted into a prostatic portion of male urethra. The stents include a removal feature or mechanism to allow for easy removal of the stent from a urethra of a patient. For example, in one embodiment, a stent includes a collapsible proximal end portion that can be biased into an expanded configuration while disposed within a prostatic urethra, and then moved to a collapsed configuration for removal of the stent from the urethra of the patient. In another embodiment, a stent includes a tapered proximal end portion with a generally fixed tapered shape that is not designed to be collapsed in the same manner as the former embodiment. With both embodiments, the a smaller leading proximal end is realized and allows for easy removal of the stent from the urethra of the patient.

The terms proximal and distal require a point of reference. In this application, the point of reference is the perspective of the operator (e.g., surgeon, physician, nurse, technician, etc.) who would insert the disclosed medical device into the patient. Therefore, the term proximal will always refer to an area closest to the operator, whereas distal will always refer to an area away from the operator. The end of the stent inserted first inside a patient's body would be the distal end of the stent, and the end of the stent closest to the operator and to an exterior incision or opening in the patient's body would be the proximal end of the stent. The patient can be a male human or some other mammal.

As mentioned above, in one embodiment according to the invention, a urinary stent includes an elongate member that defines a lumen extending therethrough and is configured to be disposed at least partially within a prostatic portion of a urethra of a patient. The elongate member includes a collapsible portion disposed at a proximal end portion of the elongate member. The collapsible portion has a first configuration in which an outer perimeter at a proximal end of the collapsible portion is substantially equal to an outer perimeter of a remaining portion of the elongate member. The collapsible portion also has a second configuration in which the outer perimeter at the proximal end of the collapsible portion is smaller than the outer perimeter of the remaining portion of the elongate member.

In this first embodiment, the collapsible portion of the elongate member can define an opening at the proximal end of the collapsible portion, where the opening is in communication with the lumen defined by the elongate member. The opening will be substantially open when the collapsible portion is in the first configuration, and the opening will be at least partially closed when the collapsible portion is in the second configuration. Also, a second portion of the urinary stent can extend from the elongate member of the stent opposite the collapsible portion of the stent's elongate member, and this second portion can be configured to be disposed at least partially within a bladder of the patient.

In a second embodiment according to the invention, a tapered proximal end portion is used in place of the first embodiment's collapsible portion. That is, in the second embodiment, the elongate member of the urinary stent includes a tapered proximal end portion that defines a fixed opening. This opening is in communication with the lumen of the elongate member to facilitate fluid flow therethrough. A second portion can extend from the elongate member opposite the tapered proximal end portion, and this second portion can be configured to be disposed at least partially within a bladder of the patient.

The use of stents or other types of endoluminal mechanical support devices to keep a duct, vessel or other body lumen open is one type of therapy for treating lumen stenosis or lumen obstruction. To treat lumen stenosis either a permanent or temporary stent can be used. A permanent stent is typically disposed within a body lumen for an indeterminate time period. A temporary stent is typically used to hold a body lumen open for a limited period of time to maintain the patency of the lumen, for example, after trauma to a lumen caused by a surgical procedure or injury.

A prostatic stent is a temporary stent in that it is typically used to keep the prostatic lobes apart, preventing the compression of the urethra and allowing the flow of fluid (e.g., urine) therethrough. For example, a prostatic stent may be desired after different types of prostatic thermal therapy methods such as, for example, Visual Laser Ablation of the Prostate (VLAP), Transurethral Microwave Thermotherapy (TUMT), Transurethral Ultrasound-Guided Laser Incision of the Prostate (TULIP), Interstitial Laser Coagulation (ILC), Transurethral Needle Ablation (TUNA), HIFY, cryosurgery, etc., to treat benign prostatic hyperplasia. Such stents can also be used in provisional treatment of patients with urinary retention prior to prostatic surgery, or to test the effect of surgical treatment in the case of lower urinary tract obstruction induced by benign prostatic hyperplasia. As the oedema (i.e., build up of excess fluid) subsides, the stent can be withdrawn. Typical removal procedures include the pulling of a suture or tether coupled to the stent. Stents and methods to remove such stents are described herein that reduce or eliminate discomfort to the patient during the removal process.

FIG. 1 is a schematic illustration of a urinary stent (also referred to herein as "prostatic stent" or "stent" or "urethral stent", for example) according to an embodiment of the invention shown disposed within a schematic illustration of a male urinary system. The anatomy of the male urinary system shown in FIG. 1 includes a urethra 50 (also referred to herein as "penile urethra"), an external sphincter 52, an opening to the external sphincter 54, a prostate 56, a prostatic section of the urethra 58 (also referred to herein as "prostatic urethra"), a bladder neck sphincter 60 and a bladder 62. The point of insertion of a prostatic stent is through the meatus 64.

A prostatic stent 20 includes an elongate member 22 that is sized to be at least partially disposed within the prostatic urethra 58. For example, the elongate member 22 can have an outer perimeter sized to maintain the prostatic urethra 58 in an open state. The elongate member 22 defines a lumen (not shown) extending between a proximal end and a distal end of the elongate member 22 to facilitate fluid (e.g., urine) flow therethrough. The elongate member 22 can be a variety of different configurations. For example, the elongate member 22 can be coiled or have an accordion shape. The elongate member 22 can also be formed with a flexible material to allow it to accommodate bodily movements.

The elongate member 22 also includes a proximal end portion 24 that can be used to provide easy removal of the stent 20 from the prostatic urethra and urethra. For example, the proximal end portion 24 can be shaped to provide for a tapered removal end. In some embodiments, the proximal end portion 24 can be moved from a first configuration in which the proximal end portion 24 has a an outer perimeter substantially the same as an outer perimeter of a remaining portion of the elongate member 22, to a second configuration in which the proximal end portion 24 has an outer perimeter smaller than the outer perimeter of the remaining portion of the elongate member 22. The proximal end portion 24 can be formed monolithically with the elongate member 22, or can be a separate component coupled to the elongate member 22. The various embodiments of the proximal end portion 24 are described in more detail below with reference to specific embodiments.

A tether 32, such as a suture, is coupled to the proximal end portion 24 and extends out through the urethra 50. The tether 32 can be used to urge the stent 20 proximally for removal of the stent 20 from the patient's body. A bead member 34 can be coupled to the tether 32 as shown in FIG. 1. The bead member 34 can prevent a proximal end portion of the tether 32 from being pulled distally into the urethra 50. The bead member 34 can be a variety of different shapes and sizes and can, in some embodiments, be slidably coupled to the tether 32.

The prostatic stent 20 also includes a retaining member 28 extending distally from the elongate member 22, and a distal tip portion 30. As with the proximal end portion 24, the retaining member 28 can be formed monolithically with the elongate member 22, or be a separate component coupled to the elongate member 22. Likewise, the distal tip portion 30 can be formed monolithically with the retaining member 28 or provided as a separate component coupled thereto. The retaining member 28 is configured to be disposed within the bladder 62 and prevent the elongate member 22 from being moved proximally out of the prostatic urethra 58. For example, fluid pressure within the bladder 62 and prostatic urethra 58 can exert pressure on the elongate member 22 urging it proximally. The retaining member 28 can be a variety of different shapes, sizes and configurations. For example, possible embodiments of a retaining member include umbrella shaped prongs and a pigtail curl. Retaining member embodiments are typically at least partially collapsible or able to be straightened for insertion into a body lumen.

In some embodiments, a retaining member is not required, for example, if a prostatic stent includes another means to prevent migration of the prostatic stent from the prostatic section of the urethra (for example, an elongate member that frictionally engages the patient's prostate section of the urethra). The distal tip portion 30 is also configured to be disposed within the bladder 30. The distal tip 30 can be shaped and/or sized to help insert the stent within the urinary system. For example, the distal tip 30 can be tapered from a proximal end to a distal end of the distal tip 30. The distal tip 30 can also be curved or have a coude shape.

Having described above various general examples, several examples of specific embodiments are now described. These embodiments are only examples, and many other configurations of a stent 20 are contemplated.

FIGS. 2-5 illustrate a prostatic stent according to a first embodiment of the invention. A urinary stent 120 includes an elongate member 122, a retaining member 128, and a distal tip portion 130. The elongate member 122 defines a lumen 144 (see FIGS. 4 and 5) that extends from a proximal end 138 to a distal end 146 to facilitate the flow of fluid therethrough. In this embodiment, the retaining member 128 has a collapsed configuration for insertion of the stent 120 into, for example, a urethra, and an expanded configuration to anchor or retain the stent 120 in position within the urethra. For example, the retaining member 128 can be pre-set or biased into the expanded configuration and moved to the collapsed configuration with use of, for example, a pusher device (shown in FIG. 6). The distal tip portion 130 is curved to help with insertion and maneuvering the stent 120 through a urinary system (e.g., through a urethra and into a bladder). The distal tip portion 130 also defines an opening 148 and a lumen (not shown) extending therethrough.

The retaining member 128 can be collapsed prior to insertion into a urethra using a pusher device as mentioned above, or with the use of other known actuating devices. For example, a pusher device can be inserted through the lumen 144 of the elongate member 122, through an interior region defined by the retaining member 128, and into the lumen of the distal tip portion 130. The pusher device can be used to collapse the retaining member 128 by applying a distal force with the pusher device as described in more detail below.

Figure 2:
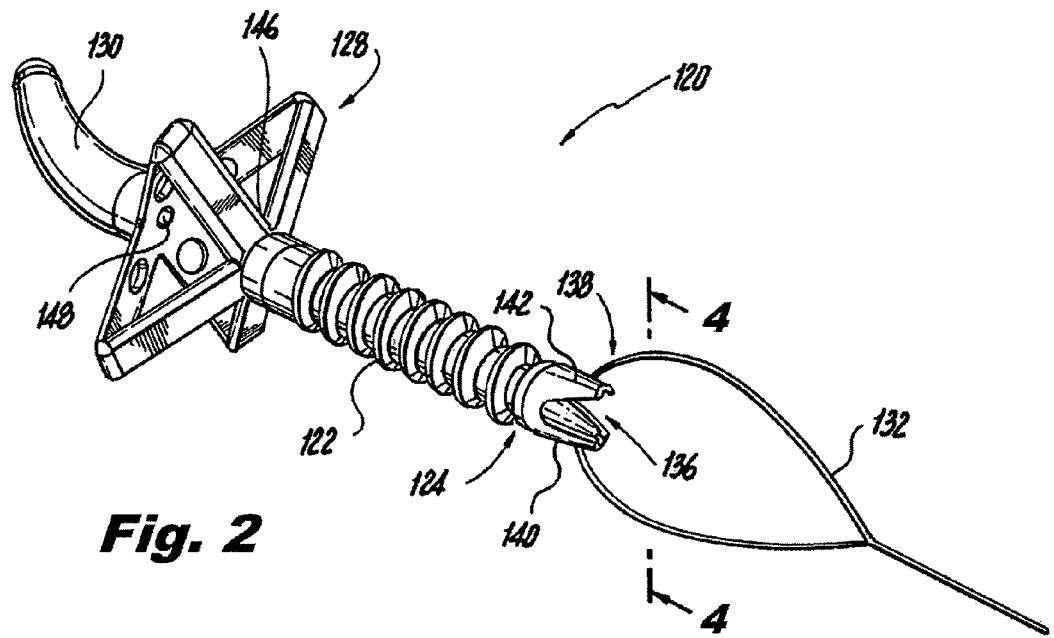
FIG. 2 is a side perspective view of a stent according to an embodiment of the invention shown with a proximal end portion in an expanded configuration.
Figure 3:
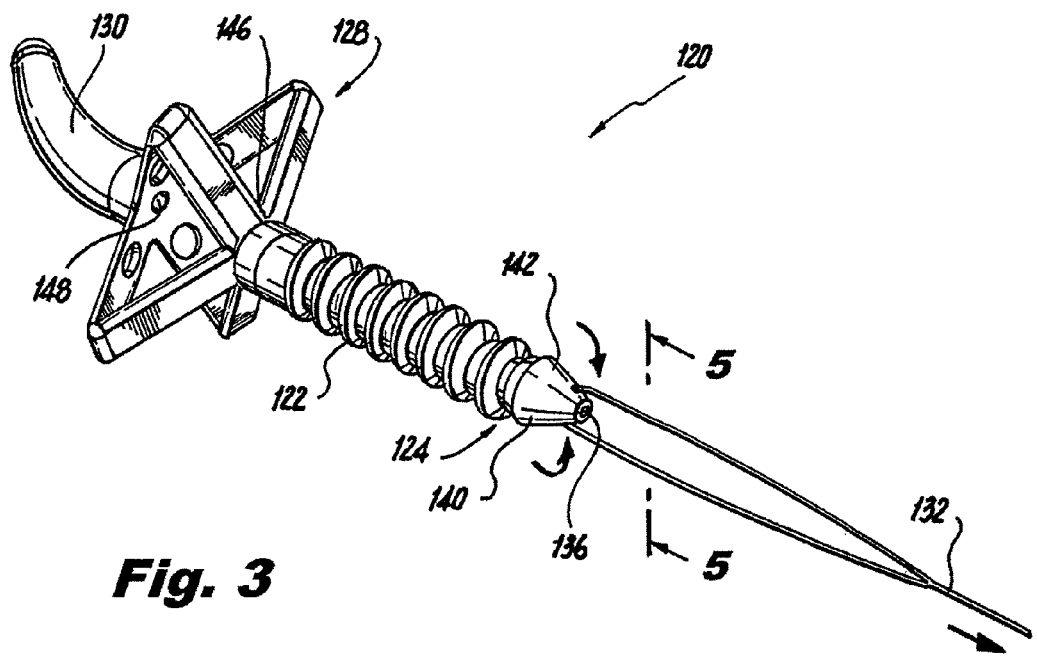
FIG. 3 is a side perspective view of the stent of FIG. 2, shown with the proximal end portion in a collapsed configuration.

The elongate member 122 can be formed with a flexible material and have an accordion-type configuration, as shown in FIGS. 2 and 3, to allow the elongate member 122 to be easily maneuverable within a urethra and to accommodate for bodily movements. The elongate member 122 includes a proximal end portion 124 that includes a pair of arms 140 and 142 that collectively define an opening 136 at the proximal end 138 of the elongate member 122. Although two arms are shown, in alternative embodiments, the proximal end portion 124 can include more than two arms.

Figure 4:
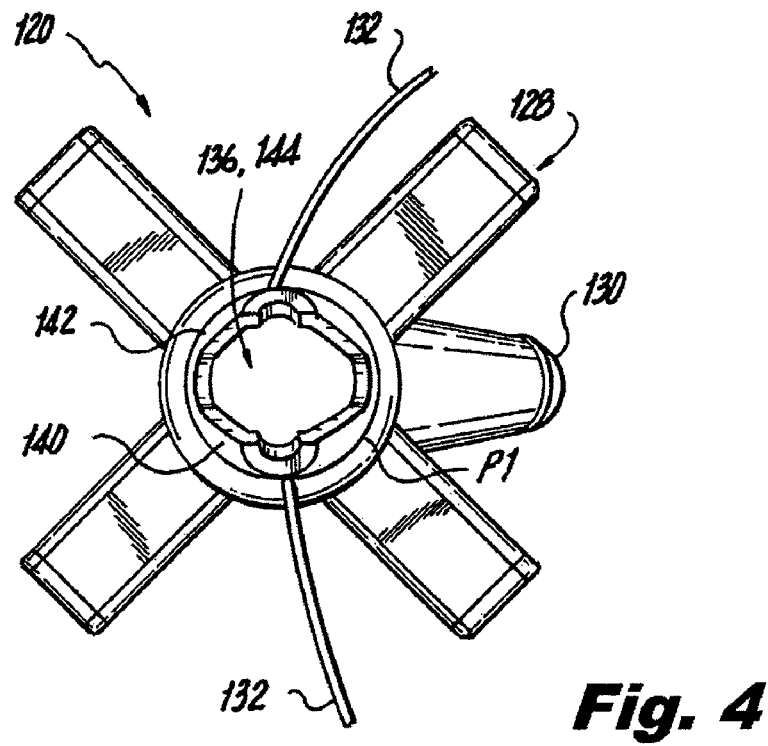
FIG. 4 is a proximal end view of the stent of FIG. 2 taken along line 4-4 in FIG. 2.
Figure 5:
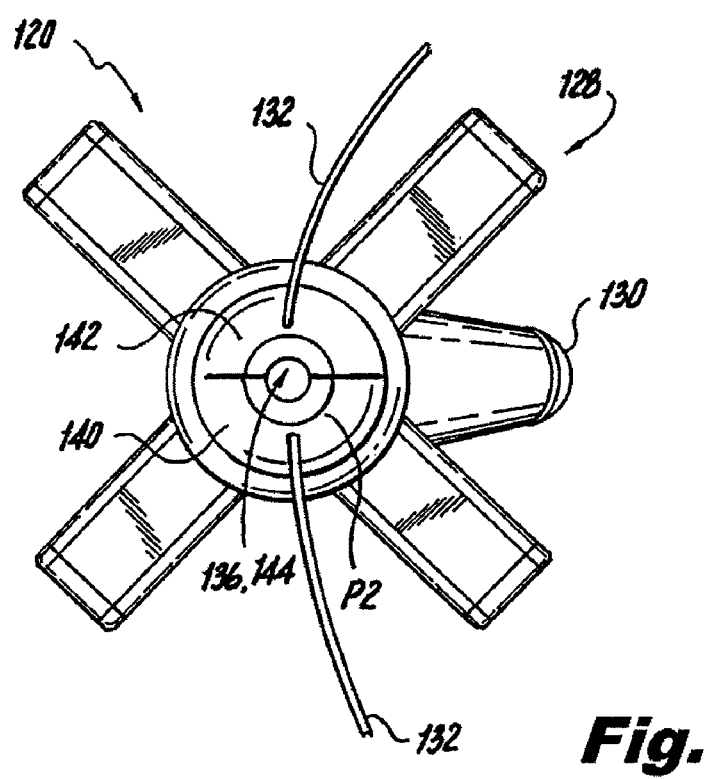
FIG. 5 is a proximal end view of the stent of FIG. 3 taken along line 5-5 in FIG. 3.

The proximal end portion 124 has an expanded or open configuration, as shown in FIGS. 2 and 4, and a collapsed or substantially closed configuration, as shown in FIGS. 3 and 5. For example, the arms 140 and 142 can be formed with a shape-memory material and biased into the expanded configuration. The arms 140 and 142 can then be moved to the collapsed configuration by urging the arms 140 and 142 toward each other. A tether 132 is coupled to each of the arms 140 and 142 and used to urge the arms 140 and 142 toward each other.

When the proximal end portion 124 is in the expanded configuration, the opening 136 defined by the arms 140 and 142 is a first size or diameter as shown in FIG. 4. When the proximal end portion 124 is in the collapsed configuration, the opening 136 defined by the arms 140 and 142 is a second size or diameter that is smaller than the first size of the opening 136, and the proximal end portion 124 forms a frusto-conical shape, as shown in FIGS. 3 and 5. Also shown in FIGS. 4 and 5, when the proximal end portion 124 is in the expanded configuration (FIG. 4), an outer perimeter P1 at the proximal end 138 is greater than an outer perimeter P2 at the proximal end 138 when the proximal end portion 124 is in the collapsed configuration (FIG. 5). The outer perimeter P1 is substantially equal to an outer perimeter of the remaining portion of the elongate member 122. While the stent 120 is disposed within a urinary system of a patient, the proximal end portion 124 maintains the expanded configuration to hold open the prostatic urethra and allow for fluid flow through the elongate member 122 and urethra. The smaller outer perimeter P2 of the proximal end portion 124 in the collapsed configuration provides a lower profile configuration to assist with the removal of the stent 120 from the prostatic urethra and urethra.

As stated above, prior to insertion of the stent 120 into a male urinary system of a patient, the retaining member 128 is moved to the collapsed configuration using, for example, a pushing device 166, as shown in FIGS. 6 and 7. FIG. 6 is a side view of a pushing device 166, and FIG. 7 is a side view of the stent 120 with the retaining member 128 collapsed using the pushing device 166. To collapse the retaining member 128 using the pushing device 166, a physician can hold the tether 132 while applying a force in a distal direction (e.g., in a direction of arrow A shown in FIG. 7).

The pushing device 166 includes a handle 168, and has a distal end 170 and a proximal end 172. A width of the pushing device 166 is sized to fit within the lumens of the prostatic stent 120 (e.g., within the lumen of the elongate member 122, the interior region of the retaining member 128 and the lumen of the distal tip portion 130). A length of the pushing device 166 is sized so that the distal end 170 can contact an interior wall of a distal end 178 of the distal tip portion 130, while the proximal end 172 and handle 168 extend outside of the patient's body. The pushing device 166 can be made from any material that is flexible enough to conform to the patient's anatomy, but also rigid enough to extend the distal tip portion 130 away from the elongate member 122. Materials such as stainless steel or polycarbonate meet these criteria.

The pushing device 166 can be curved, as shown in FIG. 6, or straight (not shown), to accommodate the particular configuration of the stent 120 and to aid in the insertion and placement of the prostatic stent 120 within the prostatic portion of the urethra. In some embodiments, the pushing device 166 can include a lumen extending through the pushing device 166 capable of receiving a guide wire. The proximal end 172 of the pushing device 166 is coupled to the handle 168.

Figure 8:
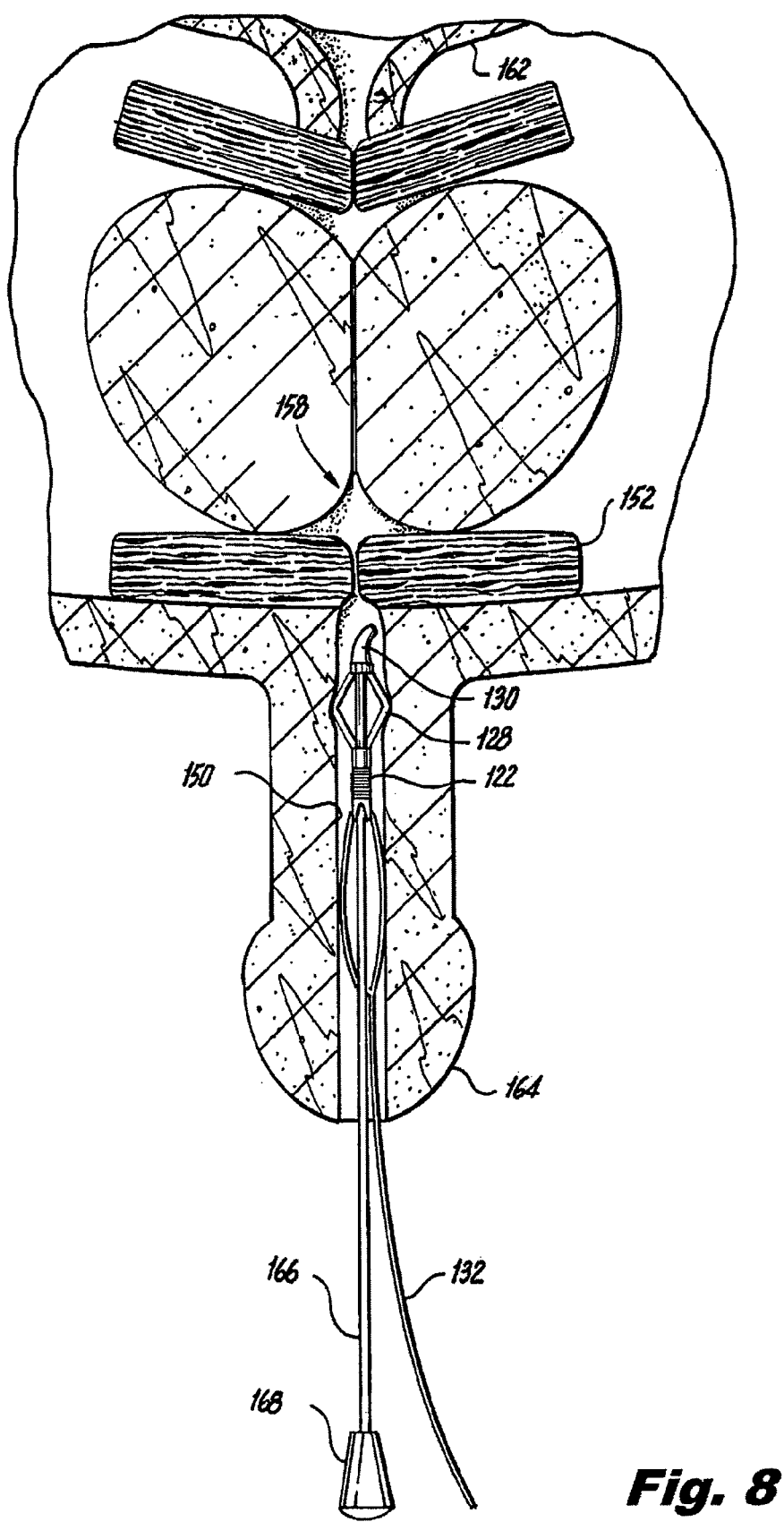
FIG. 8 is a side view of the stent of FIGS. 2-5 shown in a collapsed configuration and being inserted through a schematic illustration of a male urinary system.
Figure 9:
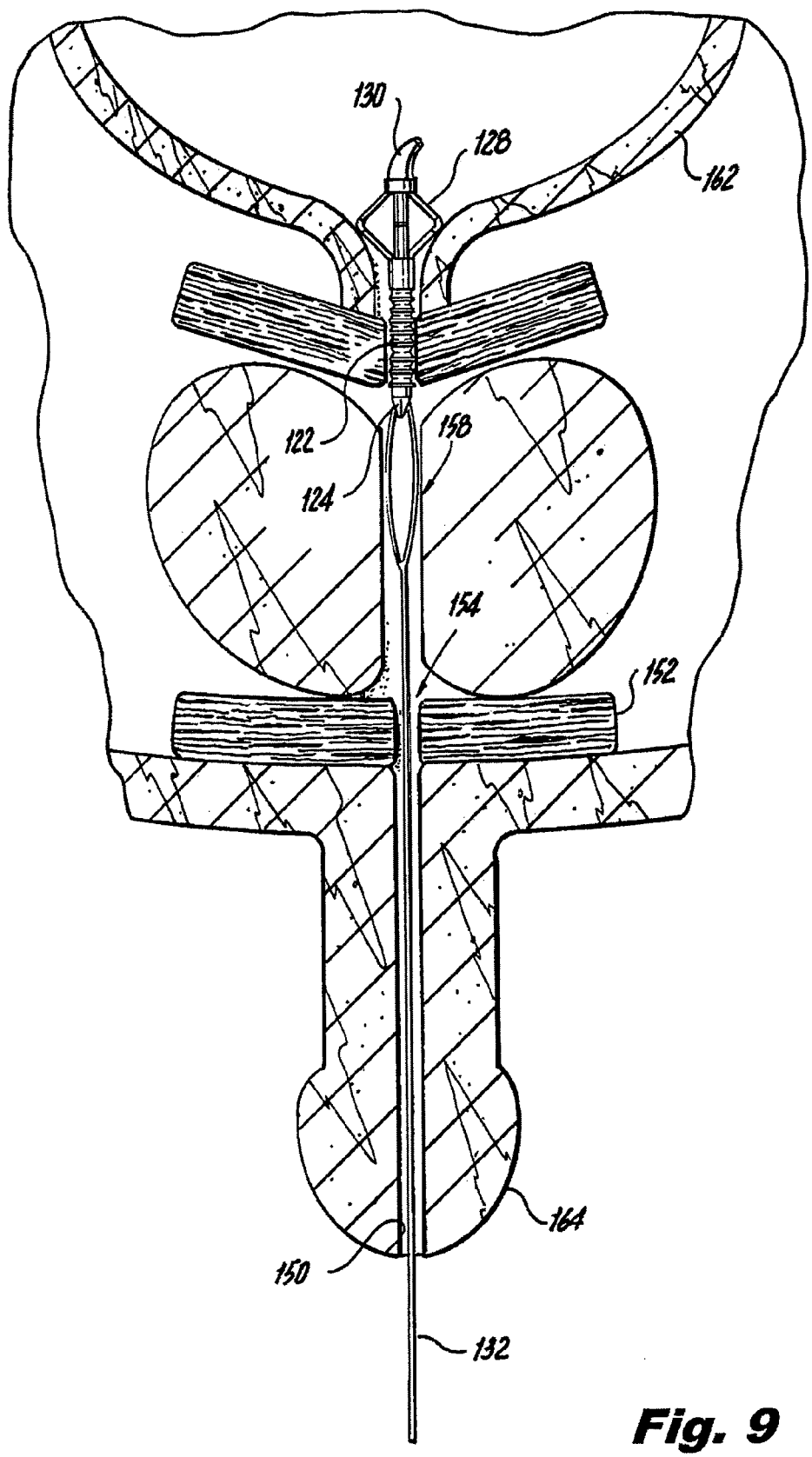
FIG. 9 is a side view of the stent of FIGS. 2-5 shown in an expanded configuration and inserted within a male urinary system.

FIGS. 8 and 9 illustrate the insertion of the stent 120 into a male urinary system using the pushing device 166. As illustrated in FIG. 8, with the retaining member 128 in the collapsed configuration, the physician inserts the stent 120 through the meatus 164. As stated above, to maintain the retaining member 128 in the collapsed configuration, the physician holds the tether 132 while applying a distal force to the pushing device 166. The stent 120 is advanced through the urethra 150 until the distal tip portion 130 and retaining member 128 are positioned within the bladder 162, and the elongate member 122 is positioned at least partially within the prostatic urethra 158. As the stent 120 is being inserted through the urethra 150, the proximal end portion 124 will be partially collapsed due to the pulling on the tether 132 during insertion of the stent 120. After being properly placed within the urinary system, the physician can release the tether 132 and remove the pushing device 166. This will allow the retaining member 128 and the proximal end portion 124 to each be moved back to their respective biased expanded configurations, as shown in FIG. 9.

The prostatic stent 120 can remain inside the male urinary system to prevent bladder outlet obstruction and to promote prostate recovery. With the stent 120 disposed within the external sphincter opening 154 will contract, allowing the external sphincter 152 to operate normally and thus allowing the patient to control bladder functions even though the prostatic stent 120 remains in place. The tether 132 attached to the proximal end portion 124 extends through the urethra 150 and terminates just outside the meatus 164, or can alternatively have a length sized to terminate within the urethra 150, just inside the meatus 164. The tether 132 is thin enough to pass through the contracted external sphincter opening 154 without negatively impacting the operation of the external sphincter 152, or therefore the patient's bladder control.

To remove the stent 120 from the urinary system (for example, at a later time), the physician can pull proximally on the tether 132. This action will cause the arms 140 and 142 of the proximal end portion 124 to be urged toward each other, and move the proximal end portion 124 to its collapsed configuration (as shown in FIGS. 3 and 5). As the stent is pulled proximally, the retaining member 128 will at least partially collapse as it is pulled through the bladder neck sphincter 160, prostatic urethra 158 and urethra 150 due to lateral forces on the retaining member 128. The physician continues to pull on the tether 132 until the stent 120 is removed from the patient's body.

In some embodiments, prior to removing the stent 120 from the patient, the pushing device 166 can optionally be inserted back into the stent 120 to move the retaining member 128 back to its collapsed configuration. In such a case, while holding the tether 132, the physician can insert the pushing device 166 into the stent 120, moving the retaining member 128 to its collapsed configuration. The physician can then pull the tether 132 and pushing member 166 proximally to remove both from the patient.

In some embodiments, a guide wire (not shown) can be used to assist in guiding the stent through the urinary system. For example, a stent (as described herein) can optionally include an opening on a distal end through which a guide wire can be inserted. In such embodiments, the pushing device used to insert the stent can also include a lumen extending therethrough, and an opening on a distal end. The guide wire can be inserted through a urethra and into a bladder of a patient. The pushing device can then be used as described above to move a retaining member of the stent to a collapsed configuration. After the guide wire is in position within the urinary system, the stent (with the pushing device disposed therethrough) can be inserted into the urethra and advanced into the bladder using the guide wire as a guide to assist in placement of the stent. For example, the lumen of the pushing device can be distally moved over the guide wire. After the stent is positioned in a desired location, the guide wire and pushing device are removed. The guide wire can alternatively be placed through the lumen of the pushing device prior to inserting the guide wire into the urinary system.

In some embodiments, a delivery sheath (not shown) can be used in conjunction with a pushing device to place the stent 120 within a male urinary system. In such an embodiment, the sheath can be placed over the elongate member 122 and tether 132 such that a distal end of the sheath contacts a proximal end of the retaining member 128. The sheath can be used to push the stent 120 distally through the urethra. Once the stent 120 is properly placed, with the retaining member 128 disposed within the bladder and the elongate member 122 at least partially disposed within the prostatic portion of the urethra, the sheath can be removed along with the pushing device.

Figure 10:
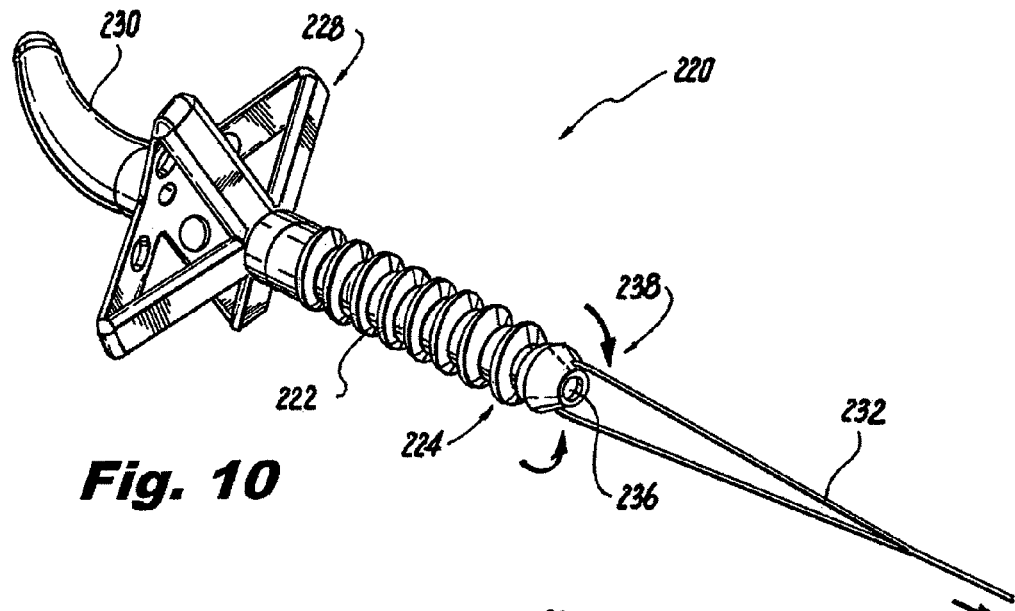
FIG. 10 is a side perspective view of a stent according to another embodiment of the invention.

A second disclosed embodiment of a prostatic stent having a proximal end portion configured for easy removal of the stent is illustrated in FIG. 10. In this second embodiment, a urinary stent 220 is similarly constructed as the previous/first disclosed embodiment, and can be positioned within a male urinary system in a similar manner. The stent 220 includes an elongate member 222 that defines a lumen (not shown in FIG. 10) that extends therethrough and an opening 236 at a proximal end 138 of the elongate member 222. The elongate member 222 includes a proximal end portion 224 that tapers toward a proximal end 238 of the elongate member 222. The tapered proximal end portion 224 provides a relatively small profile leading edge for easier removal of the stent 220 from a urethra of the patient in a similar manner as described above. The shape of the tapered proximal end portion 224 can be frusto-conical. A tether 232 can be coupled to the proximal end portion 224 and used to pull the stent 220 proximally out of the patient's body.

Figure 11:
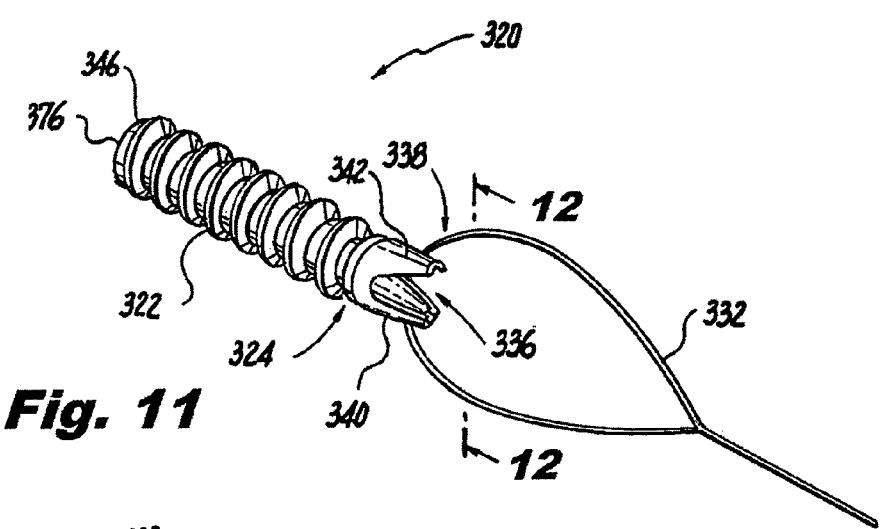
FIG. 11 is a side view of a stent according to another embodiment of the invention.

FIG. 11 illustrates a stent according to an embodiment of the invention that does not include a collapsible retaining member (e.g., 128, 228) for placement in at least part of the bladder of the patient. Instead of the retaining member, in this alternative embodiment, a stent 320 includes an elongate member 322 that is sized to frictionally engage a prostatic portion of a urethra to retain the elongate member 322 in position within the prostatic urethra. The elongate member 322 defines a lumen 344 extending between a proximal end 338 and a distal end 346, and openings 336, and 374 on the proximal end 338 and distal end 346, respectively. The elongate member 322 also includes a proximal end portion 324 having collapsible arms 340 and 342 similar to the proximal end portion 124 described above. This stent of FIG. 11 is a variation of the first disclosed embodiment of a urinary stent according to the invention that has a collapsible proximal end portion that allows easy removal of the stent from the patient.

Figure 12:
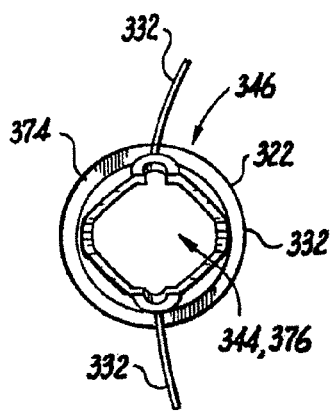
FIG. 12 is a distal end view of the stent of FIG. 11.

In this embodiment shown in FIG. 11, the stent 320 can be inserted into a urinary system using a pushing device (not shown) that includes a radially extending flange at a distal end. When the pushing device is inserted through the lumen 344 of the elongate member 322, the flange of the pushing device engages a corresponding flange 374 (see FIG. 12) on the distal end 346 of the elongate member 322 to push the stent 320 distally through a urethra. A tether 332 coupled to the proximal end portion 324 is used to collapse the proximal end portion 324 as described above with reference to stent 120, to remove the stent 320 from the patient.

Figure 13:
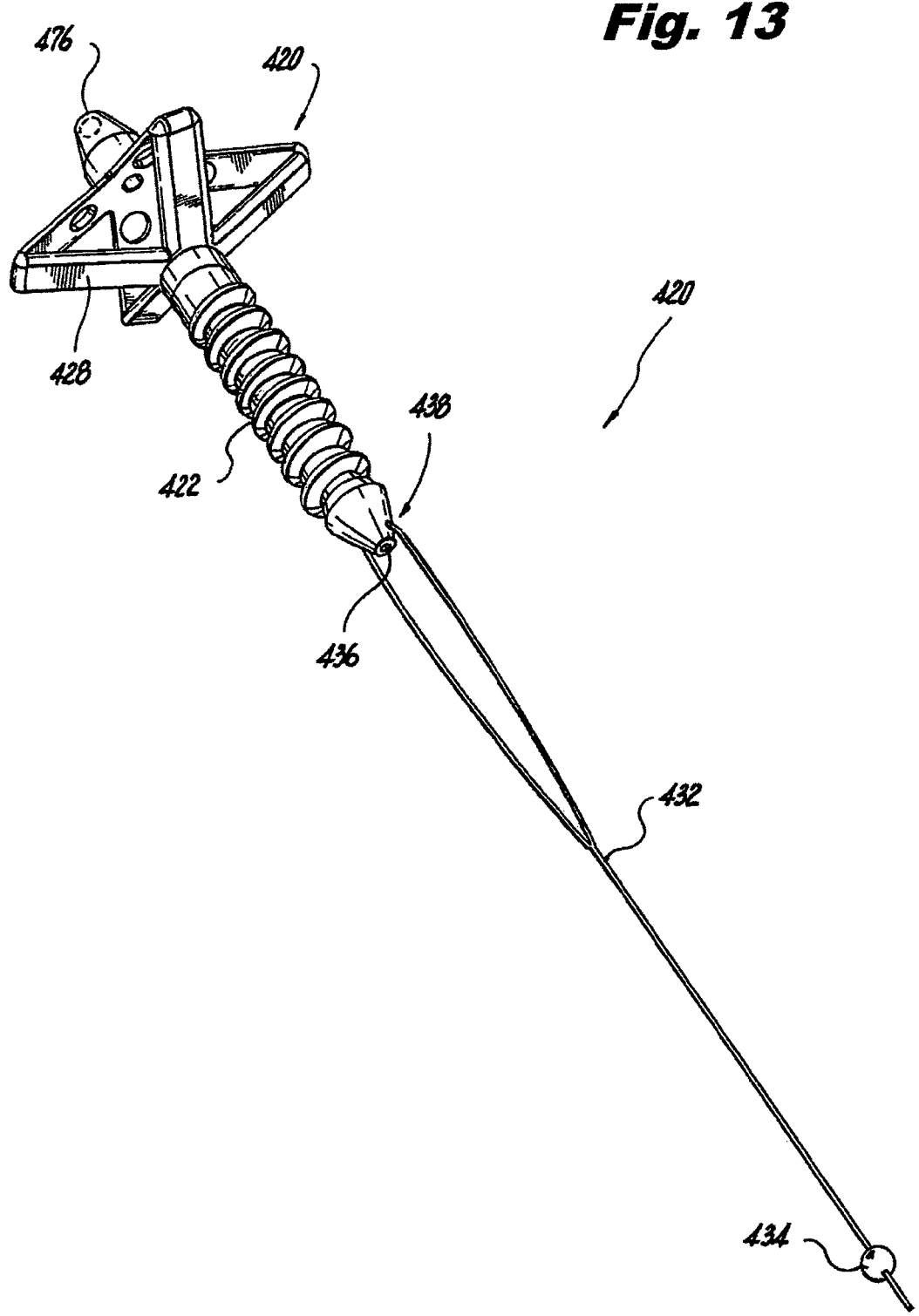
FIG. 13 is a side view of a stent according to another embodiment of the invention.

FIG. 13 illustrates a stent similar to the second disclosed embodiment stent 220 of FIG. 10, except with an opening 476 at a distal end for receiving a guide wire therethrough. The stent 420 includes an elongate member 422 and a collapsible retaining member 428. The elongate member 422 has a proximal end portion 424 that is tapered toward a proximal end 438 of the elongate member 422, and defines an opening 438. A tether 432 is coupled to the proximal end portion 424 and used for removal of the stent 420 as described above for previous embodiments. In this embodiment, a bead member 434 is also coupled to the tether 432.

The two main disclosed embodiments of urinary stents according to the invention (referred to and shown here generally as 120 and 220), as well as the other disclosed embodiments (e.g., 20, 320, and 420) can be constructed with any suitable material used for such medical devices. For example, the various components of a stent can be formed with one or more biocompatible materials, such as silicone, nylon, polyglycolic acid, or stainless steel, and various polymers. The various components of a stent according to the invention can be formed with various elastic materials, flexible materials, rubber materials, or combinations thereof. In addition, various components, such as the collapsible portion (e.g., 124, 324) and the retaining member (e.g., 128, 228, 428) can each be formed with a shape-memory material such as nitinol or super-nitinol, where nitinol is a trademark standing for a nickel-titanium alloy material.

All disclosed embodiments are examples and are not limiting or restrictive on the invention. Also, while certain embodiments and related methods have been particularly shown and described, various changes in form and details may be made and are included herein. For example, the collapsible portion and the retaining member can each be moved between their collapsed and expanded configurations by means other than those described herein such as by hinges or other mechanisms. Also, various different types of delivery devices can be used to insert and/or remove a urinary stent into/from the body of a patient. Further, the distal tip portion, the retaining member, the elongate member, and the collapsible portion can have a variety of different shapes and sizes. A retaining member can be, for example, an expandable balloon or other type of expandable member configured to maintain the elongate member in position within a urinary system.

What is claimed is:

1. A urinary stent comprising an elongate member, the elongate member defining a lumen extending from a proximal end to a distal end of the elongate member, the proximal end comprising a proximal tip configured to be disposed within a prostatic portion of a urethra of a patient, the proximal end comprising a first arm and a second arm disposed opposite the first arm, the first and second arms defining an opening at the proximal tip of the proximal end, the first and second arms being biased in an expanded configuration in which the opening has a diameter that is substantially equal to an outer diameter of a remaining portion of the elongate member, and movable into a collapsed configuration in which the diameter of the opening is smaller than the outer diameter of the remaining portion of the elongate member.

2. The urinary stent of claim 1 wherein the collapsed configuration forms a frusto-conical shape terminating at the proximal tip of the proximal end of the elongate member.

3. The urinary stent of claim 1 wherein the first and second arms are formed monolithically with the elongate member.

4. The urinary stent of claim 1 further comprising a second portion extending from the distal end of the elongate member and configured to be disposed at least partially within a bladder of the patient.

5. The urinary stent of claim 1, further comprising a tether coupled to each of the first and second arms for moving the first and second arms towards each other into the collapsed configuration.

6. A urinary stent, comprising:
an elongate member defining a lumen extending from a proximal end to a distal end of the elongate member, the proximal end comprising a proximal tip configured to be disposed within a prostatic portion of a urethra of a patient, the proximal end comprising a first arm and a second arm disposed opposite the first arm, the first and second arms defining an opening at the proximal tip of the proximal end, the opening in fluid communication with the lumen, the first and second arms being biased in an expanded configuration in which the opening has a first diameter that is substantially equal to an outer diameter of the remaining portion of the elongate member, and movable into a collapsed configuration in which the diameter of the opening is smaller than the outer diameter of the remaining portion of the elongate member; and a second portion extending from the distal end of the elongate member and configured to be disposed at least partially within a bladder of the patient.

7. The urinary stent of claim 6 wherein the collapsed configuration forms a frusto-conical shape terminating at the proximal tip of the proximal end of the elongate member.

8. The urinary stent of claim 6 wherein the first and second arms are formed monolithically with the elongate member.

9. The urinary stent of claim 6 wherein the second portion has a collapsed configuration for insertion into the bladder, and an expanded configuration for retaining the second portion within the bladder.

10. The urinary stent of claim 6, further comprising a tether coupled to each of the first and second arms for moving the first and second arms towards each other into the collapsed configuration.

* * * * *